United States Patent
Kennedy

(10) Patent No.: US 8,071,138 B2
(45) Date of Patent: Dec. 6, 2011

(54) PRODUCT AND COMPOSITION FOR ALLEVIATING POST-MENSTRUAL SYMPTOMS

(76) Inventor: Lina Kennedy, Los Angeles, CA (US)

( * ) Notice: Subject to any disclaimer, the term of this patent is extended or adjusted under 35 U.S.C. 154(b) by 190 days.

(21) Appl. No.: 12/487,983

(22) Filed: Jun. 19, 2009

(65) Prior Publication Data

US 2009/0324753 A1  Dec. 31, 2009

Related U.S. Application Data

(60) Provisional application No. 61/073,798, filed on Jun. 19, 2008.

(51) Int. Cl.
*A01N 65/00* (2009.01)
(52) U.S. Cl. ........................................ 424/725
(58) Field of Classification Search ................. None
See application file for complete search history.

(56) References Cited

OTHER PUBLICATIONS

Nyakabwa et al, Plantes medicinales cultivees dans la zone de Kabondo a Kisangani (Zaire) African Study Monographs, col. 11, No. 2, Jan. 1990, pp. 87-99.

Lubini, A "The plants used in traditional medicine by the Yansi . . . " Assoication for the Taxonomic Study of tropical African Flora, vol. 23, Jan. 1, 1990, pp. 1007-1020.
Ajibade L T et al, "Ethnomedicine and Primary Healthcare in Ilorin, Nigeria"; Indian Journal of Traditional Knowledge; vol. 4, No. 2, Apr. 1, 2005, pp. 150-158.
Tribhubana Panda A & Rabindra N Padhy B; "Ethnomedicinal plants used by tribes of the Kalahandi district, Orissa"; vol. 7, No. 2, Apr. 1, 2008, pp. 242-249.
Tenguriya R K et al; "Report on medical potential of *Calotropis procera*"; Biosciences Biotechnology Research Asia; vol. 4, No. 2, Dec. 1, 2007, pp. 823-825.
Duke, James A. et al; "Handbook of medicinal herbs 2nd edition— *Calotropis procera*" 2002 CRC Press LLC, p. 682, col. 683.

*Primary Examiner* — Michael Meller
(74) *Attorney, Agent, or Firm* — Rick B. Yeager

(57) ABSTRACT

The current invention relates to a natural composition for topical application to skin to alleviate post-menstrual symptoms of cramping, backache, and breast tenderness; and for other aches and pains including Rheumatic, muscular and articular pains; and local treatment such as tendinitises, tennis elbow, benign distorsions, arthritis, osteoarthritis, neuralgia, sciatic nerve, lumbago, back pains, migraine, stiff neck, and insect bites. In one embodiment, the composition of the cream or lotion includes active natural ingredients of *Carapa procera* and *Calotropis procera* with shea butter and soy oil. In one embodiment the composition includes, by weight percent, 30% to 80% *Butyrospermum parkii* (Shea butter); 10% to 30% *Glycine poja* (soy); 10% to 30% *Carapa procera*; 3% to 10% *Calotropis procera*; and 3% to 10% Menthol.

5 Claims, No Drawings

PRODUCT AND COMPOSITION FOR ALLEVIATING POST-MENSTRUAL SYMPTOMS

RELATED APPLICATIONS

This application is related to U.S. provisional patent application No. 61,073,798 filed by applicant on Jun. 19, 2008, and claims priority from that application.

BACKGROUND

1. Field of Invention

The current invention relates to a natural composition for topical application to skin to alleviate post-menstrual symptoms of cramping, backache, and breast tenderness.

2. Prior Art

Prior art topical compositions have been used for the treatment of sports injuries and for massage therapy.

There is a need for products and product delivery methods which effectively address PMS discomfort.

The current invention addresses that need, by providing a natural composition which is effective for alleviating post-menstrual symptoms of cramping, backache, and breast tenderness.

SUMMARY OF INVENTION

In one embodiment of the current invention, a cream or lotion is provided. In one example, the composition of the cream or lotion includes active natural ingredients of *Carapa procera* and *Calotropis procera* with shea butter and soy oil. In other embodiments, other skin conditioners and carriers may be substituted for the shea butter and soy oil.

Applicant has found that topically-applied *Carapa procera* and *Calotropis procera* compositions provide unexpected relief of PMS symptoms including cramps and abdominal discomfort, backache, and breast tenderness.

In one embodiment, the composition is provided as an ointment, lotion, or cream that is rubbed on the skin.

In one embodiment, the composition is provided in a roll-on container so that it can be applied to the skin.

In another embodiment, the composition is provided as a spray which is sprayed on the skin.

In one embodiment, the composition is provided in dry packs that can be added to bath water.

In another embodiment, a composition is provided as a hot pack to be applied to skin after a cold bath.

DESCRIPTION OF INVENTION

PMS 4 PMS™ Ointment

The following examples are illustrative of the present invention. The components and specific ingredients are presented as being typical, and various modifications can be derived in view of the foregoing disclosure within the scope of the invention. All percentages, ratios and proportions herein are by weight, unless otherwise specified. All temperatures are in degrees Celsius unless otherwise specified.

Example 1

Cream Composition

In this example, a composition is provided from all natural ingredients, including *Carapa procera* and *Calotropis procera*.

| Ingredient | Composition Range (Weight %) |
| --- | --- |
| *Butrospermum parkii* (Shea butter) | 30% to 80% |
| *Glycine soja* (soy) | 10% to 30% |
| *Carapa procera* | 10% to 30% |
| *Calotropis procera* | 0.5% to 10% |
| Menthol | 0.5% to 10% |

Indications: The Shea butter and plants in this ointment work together to relieve many aches and pains such as external use rheumatic, muscular and articular pains; for local treatment such as tendinitis, tennis elbow, benign distorsions, arthritis, osteoarthritis, neuralgia, sciatic nerve, lumbago, back pains, menstrual pains, all massages for sportsmen (wrench, breakdown, ache), migraine, stiff neck, and insect bites.

Example directions for PMS 4 PMS are:

"As soon as you feel a cramp coming on apply a thin layer of PMS ointment to the lower abdomen from hip to hip and gently massage in. If you experience lower back pain apply to that area as well. Apply repeatedly as often as needed."

The composition may be provided in wet or dry form in a variety of packages including those example delivery package forms described below.

Example 2

Cream Composition

| Ingredient | Composition (Weight %) |
| --- | --- |
| *Vitellaria paradoxa* (Shea Butter) | 65% |
| Soybean Oil | 15% |
| *Carapa procera* oil | 15 |
| *Calotropis procera* | 0.5% |
| Menthol | 0.5% |
| Aromatic oil of *Santalum album* (for natural scent only) | |

In this example, the composition is prepared in a two step process. In the first step, a shea butter is prepared. In the second step, the shea butter is mixed with other ingredients to form the composition.

Step I: Shea Butter Preparation:

Shea Butter is a butter extracted from the kernel of *Butrospermum parkii*. This plant, also referred to as *Vitellaria paradoxa*, is native to Africa. The term butter describes a material that is a solid at room temperature, but melts at about 40 degrees Celsius.

The Shea butter preparation typically lasts about two days. The required quantity of Shea butter is added to a mixer. Water (20%), lemon juice extract (10%), and sea salt (NaCl-5%) are added to the mixer. The mixture is heated to 60-70 degrees Celsius. Once all of the ingredients have melted, activate the electric mixer which will agitate at 3000 turns per minute for 15-20 minutes. The mixture is allowed to settle for 24 hours; and water and the settled impurities are drained from the bottom of the mixer. The Shea butter is then recovered and is ready to be used as a base component for the composition of the current invention.

Step II: Composition Preparation:

In a 100 kilogram kettle, add the following ingredients in the order indicated below:

1. Shea butter preparation;
2. Soybean oil;

3. Grate and mash the required quantity of *Calotropis procera*, add to kettle and mix together;
4. Heat the kettle to 25-30 degrees Celsius and activate the agitator/mixer;
5. When the temperature of the mixture reaches 25 Celsius, add the oils of *Carapa procera* and Menthol;
6. After 20 minutes at 3000 turns per minute to obtain a homogeneous mixture, turn off heating and mixer, and let the mixture settle for 6 hours.

Usage Directions

For muscular and articular pain, apply and massage the ointment/cream intensively on all areas with pain/discomfort twice daily. Massage for 5 minutes the local area with pain and also the surrounding area.

For headache, apply the ointment/cream to the forehead, the temples and behind the ears up to the nape of the neck and gently massage.

For bronchitis discomforts, apply and massage the ointment/cream on the chest and the back morning and night.

The composition should be stored in temperatures less than 25 degrees Celsius.

PMS 4 PMS™ Roll-On Container

In this embodiment, a *Carapa procera* and *Calotropis procera* composition is provided as a roll-on product so that it can be applied more conveniently and with less mess than an ointment.

PMS 4 PMS™ Spray

In this embodiment, a *Carapa procera* and *Calotropis procera* composition is provided as a spray-on product so that it can be applied more conveniently and with less mess than an ointment. A patch may be applied after a spray on application.

PMS 4 PMS™ Dry Bath Packs

In this embodiment, a *Carapa procera* and *Calotropis procera* composition is provided as a package of dry ingredients so that the package can be added to bath water.

In another embodiment, a *Carapa procera* and *Calotropis procera* composition is provided as a package of dry ingredients including Hungarian Wellness Mud so that the package can be added to bath water.

PMS 4 PMS™ Hot Packs

In this embodiment, a *Carapa procera* and *Calotropis procera* composition is provided as packs that may be heated and applied after a cold bath.

In another embodiment, a *Carapa procera* and Calotropis procera composition is provided as Hungarian Wellness Mud packs that may be heated and applied after a cold bath.

What is claimed is:

1. A cream comprising:
   about 10% to 30% *Carapa procera*; about 0.5% to 10% *Calotropis procera*; shea butter; soybean oil and menthol.
2. The cream of claim 1 comprising about 30-80% shea butter.
3. The cream of claim 1 comprising about 10-30% soybean oil.
4. The cream of claim 1 comprising about 0.5-10% menthol.
5. The cream of claim 1 comprising
   (a) about 65% Shea butter;
   (b) about 15% soybean oil;
   (c) about 15% *Carapa procera*;
   (d) about 0.5% *Calotropis procera*; and
   (e) about 0.5% menthol.

* * * * *